(12) United States Patent
Higurashi et al.

(10) Patent No.: US 7,128,716 B2
(45) Date of Patent: Oct. 31, 2006

(54) BLOOD FLOWMETER AND SENSOR PART OF THE BLOOD FLOWMETER

(75) Inventors: Eiji Higurashi, Zama (JP); Renshi Sawada, Sayama (JP); Takahiro Ito, Setagaya-ku (JP)

(73) Assignee: Nippon Telegraph and Telephone Corporation, Tokyo (JP)

( * ) Notice: Subject to any disclaimer, the term of this patent is extended or adjusted under 35 U.S.C. 154(b) by 296 days.

(21) Appl. No.: 10/061,602

(22) Filed: Feb. 1, 2002

(65) Prior Publication Data

US 2002/0120203 A1 Aug. 29, 2002

(30) Foreign Application Priority Data

Feb. 2, 2001 (JP) ............................. 2001-026401

(51) Int. Cl.
A61B 5/02 (2006.01)
A61B 6/00 (2006.01)
G02B 6/00 (2006.01)

(52) U.S. Cl. ........................................ 600/504; 385/12
(58) Field of Classification Search ................ 600/504, 600/329–344
See application file for complete search history.

(56) References Cited

U.S. PATENT DOCUMENTS

| | | | | |
|---|---|---|---|---|
| 4,510,938 A * | 4/1985 | Jobsis et al. | ................ | 600/344 |
| 5,055,894 A * | 10/1991 | Chan | ............................ | 257/85 |
| 5,299,570 A * | 4/1994 | Hatschek | .................... | 600/479 |
| 5,444,249 A * | 8/1995 | Wong | .......................... | 250/343 |
| 5,490,506 A * | 2/1996 | Takatani et al. | ............. | 600/309 |
| 5,584,296 A * | 12/1996 | Cui et al. | .................... | 600/479 |
| 5,822,473 A * | 10/1998 | Magel et al. | ................. | 385/12 |
| 6,045,511 A * | 4/2000 | Ott et al. | ..................... | 600/504 |
| 6,119,031 A * | 9/2000 | Crowley | ...................... | 600/407 |
| 6,486,467 B1 * | 11/2002 | Speckbacher et al. | .. | 250/237 G |
| 6,501,973 B1 * | 12/2002 | Foley et al. | ................. | 600/310 |

FOREIGN PATENT DOCUMENTS

| | | |
|---|---|---|
| EP | 0 614 098 A2 | 9/1994 |
| EP | 0 771 546 A2 | 5/1997 |
| EP | 0 990 418 A | 4/2000 |
| JP | 1-160531 | 6/1989 |
| JP | 01-160531 | 6/1989 |
| JP | 03-173528 | 7/1991 |
| JP | 05-192316 | 8/1993 |
| JP | 9-55393 | 2/1997 |
| JP | 10-500027 | 1/1998 |

(Continued)

OTHER PUBLICATIONS

Fukano, H., Matsuoka, Y., "A Low-Cost Edge-Illuminated Refracting-Facet Photodiode Module with Large Bandwidth and High Responsivity", J. Lightwave Technology, vol. 18, No. 1., pp. 79-83 (2000).

(Continued)

Primary Examiner—Robert L. Nasser
(74) Attorney, Agent, or Firm—Kenyon & Kenyon LLP

(57) ABSTRACT

A sensor part of a blood flowmeter for measuring a value on blood flow in tissue of a living body is provided, in which the sensor part includes: a light emitter for emitting light to tissue of a living body; and a light detector for receiving scattered light from the tissue; a first shading block for preventing light emitted from the light emitter from directly entering the light detector; a second shading block having a predetermined gap in front of the light detector, wherein the light emitter, the light detector and the shading blocks are integrated on a semiconductor substrate.

27 Claims, 10 Drawing Sheets

FOREIGN PATENT DOCUMENTS

| | | |
|---|---|---|
| JP | 10-211176 | 8/1998 |
| JP | 11-089808 | 4/1999 |
| JP | 11-133042 | 5/1999 |
| JP | 2000-107145 | 4/2000 |
| JP | 2000-342547 | 12/2000 |
| JP | 3150911 | 1/2001 |
| WO | WO 94/10901 | 5/1994 |
| WO | WO 95/16388 | 6/1995 |

OTHER PUBLICATIONS

Watkins, Dennis and Holloway, G. Allen Jr., "An Instrument to Measure Cutaneous Blood Flow Using the Doppler Shift of Laser Light", IEEE Transactions on Biomedical Engineering, vol. BME-25, No. 1, Jan. 28-33 (1978).

Higurashi, E., Sawada, R., Ito, T., "An Integrated Laser Doppler Blood Flowmeter for a Wearable Health Monitoring System", Optical MEMS 2001, Sep. 2001, pp. 49-50.

Fujii, H., Asakura, T., Nohira, Y., Shitomi, T., "Blood Flow Observed by Time-Varying Laser Speckle", Optics Letters vol. 10, No. 3, Mar. 1985, pp. 104-106.

Anderson, R.R. et al., The Optics of Human Skin, *The Journal of Investigative Dermatology*, 77:13-19, 1981, vol. 77, No. 1, pp. 13-19.

Stern, M.D., et al., Continuous measurement of tissue blood flow by laser-Doppler spectroscopy, *Am. J. Physiol.* 323(4): H441-H448, 1977 or *Am. J. Physiol.: Heart Circ. Physiol.* 1(4): H441-H448, 1977.

\* cited by examiner

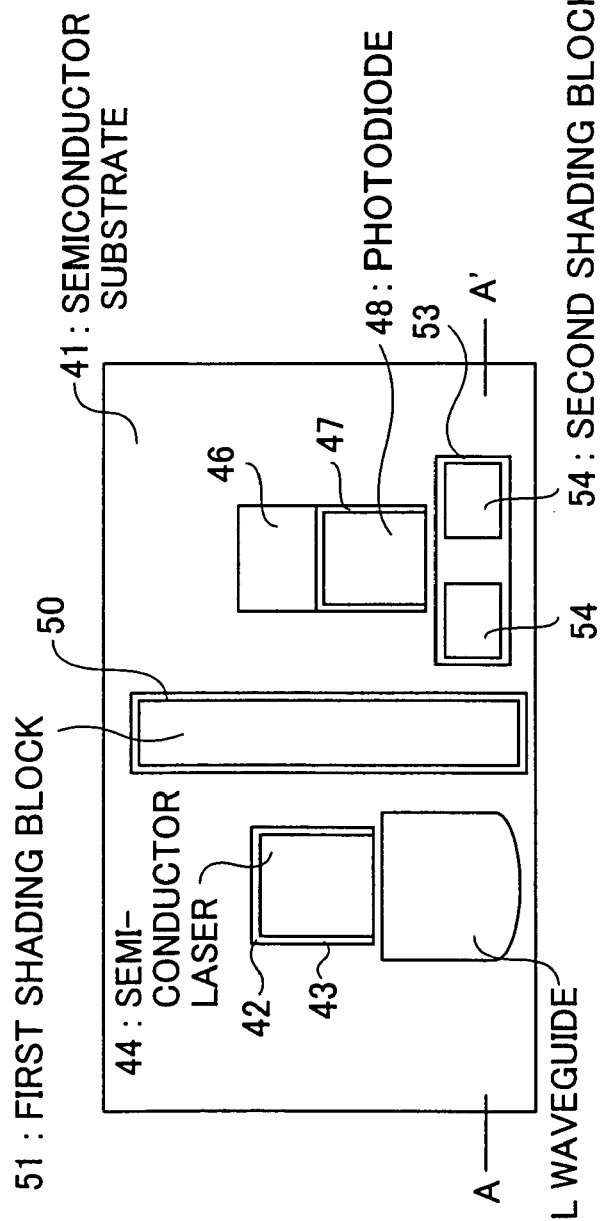

SHADING BLOCK

PHOTODIODE

SEMICONDUCTOR LASER

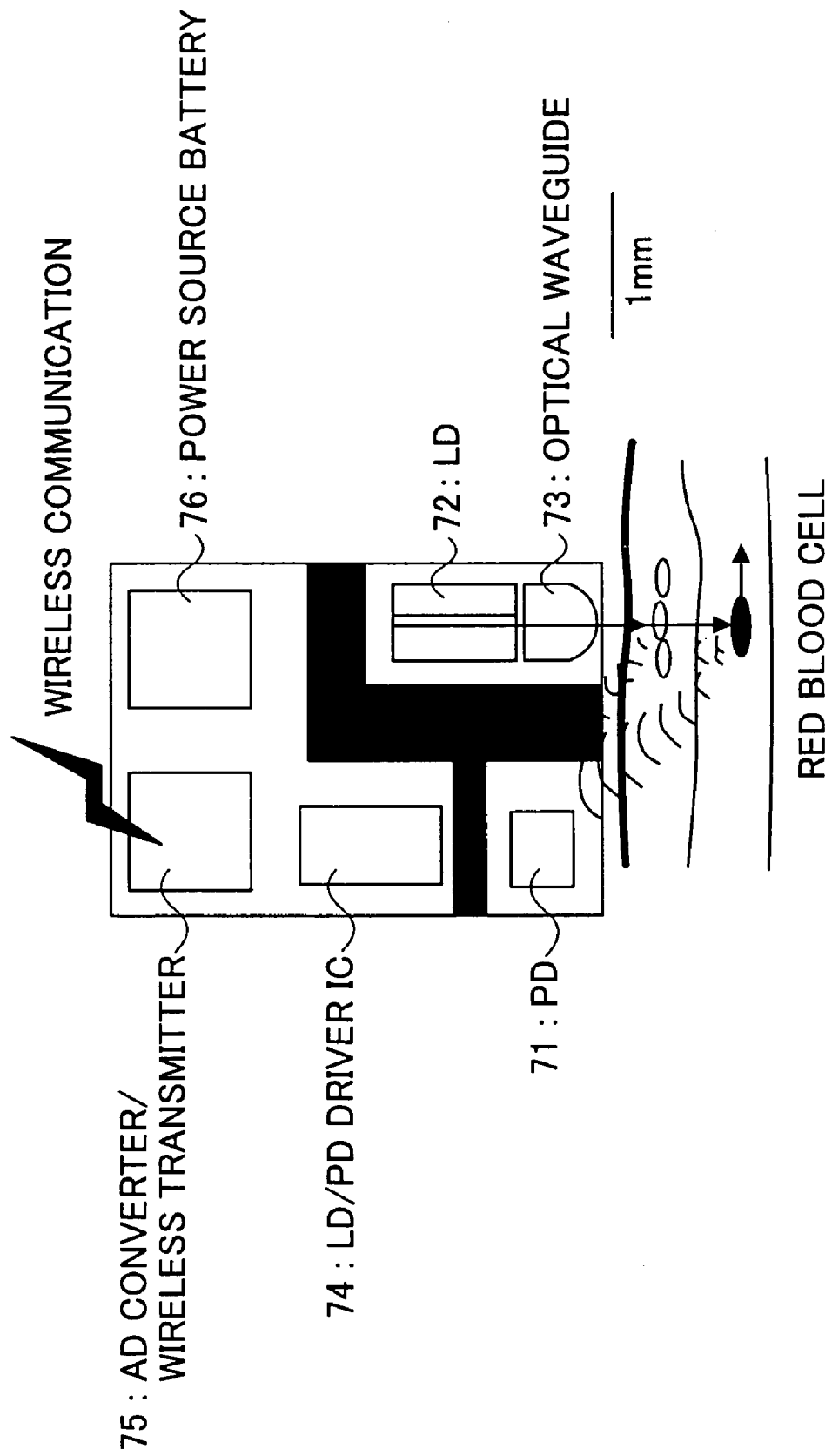

BLOOD FLOWMETER AND SENSOR PART OF THE BLOOD FLOWMETER

BACKGROUND OF THE INVENTION

1. Field of the Invention

The present invention relates to a blood flowmeter for measuring an amount of blood flow, a blood amount, a blood flow speed and a pulse of a living body by using scattered light reflected from the living body.

2. Description of the Related Art

In our aging society, there has been a growing interest to a blood flowmeter which can measure circulation of blood which closely relates to adult diseases. Especially, a laser blood flowmeter receives attention in the sense that it can measure the blood flow in capillaries of peripheral tissue without invasion since the laser blood flowmeter has much higher resolution than that of a ultrasound blood flowmeter, wherein measuring the blood flow in capillaries of peripheral tissue was difficult by the ultrasound blood flowmeter. For example, Dennis Watkins and G. Allen Holloway, Jr., An Instrument to measure cutaneous blood flow using the Doppler shift of laser light, IEEE TRANSACTIONS ON BIOMEDICAL ENGINEERING, Vol. BME-25, No. 1, Jan. 28–33 (1978) discloses a conventional blood flowmeter.

FIG. 1 shows a block diagram of the conventional blood flowmeter in the above-mentioned document. As shown in FIG. 1, a lens 2 is provided near a helium-neon laser 1 which is a light source, one end of an optical fiber 3 for floodlighting is provided near the lens 2, the other end of the optical fiber 3 is held by a holder 4, the holder 4 holds one end of the optical fiber 5 for receiving light, a photodiode 6 is provided near the other end of the optical fiber 5, a preamplifier 7 (40 Hz–40 kHz) is connected to the photodiode 6, and a signal is output via an amplifier 8. The photodiode 6 and the preamplifier 7 are a part of a measuring part for obtaining blood flow speed in tissue of a living body by receiving scattered light reflected from the tissue of the living body.

The blood flow speed is measured by the blood flowmeter shown in FIG. 1 by detecting (heterodyne detection) interference light between scattered light reflected from still tissue of the living body and scattered light reflected from red blood cells (scattered particles) which move in the capillaries in the tissue of the living body, that is, by detecting (heterodyne detection) interference light between scattered light reflected by still tissue of the living body and scattered light whose frequency is shifted due to the Doppler effect related to blood flow speed.

However, according to such a conventional blood flowmeter, since it uses optical fibers 3 and 5, it becomes large, and, since it is necessary to handle the optical fibers 3 and 5, it is difficult to attach the blood flowmeter to a living body for a long time and it is difficult to move with the blood flowmeter on. In addition, since the optical fibers 3 and 5 are provided between the helium-neon laser 1 and a subject part to be measured, the blood flowmeter is susceptible to environmental change. For example, when the optical fiber vibrates even slightly, a measurement result is affected. In addition, since the blood flowmeter is manufactured by assembling the individual optical parts such as the helium-neon laser 1, the optical fibers 3 and 5, and the photodiode 6 three-dimensionally, tuning the optical axis is necessary and manufacturing cost is high.

In addition, as conventional technologies, there are technologies disclosed in Japanese laid-open patent application No. 1-160531 "blood flow speed detector" (Hitachi), and Japanese laid-open patent application No. 10-94527 (Patent No. 3150911) "blood flow amount meter" (Biomedical Science). However, according to the technologies disclosed in these documents, there is a problem in that the degree of downsizing and the accuracy of measurement are not enough.

SUMMARY OF THE INVENTION

An object of the present invention is to provide a blood flowmeter which is not susceptible to environmental change, is manufactured at low cost, and provides high measurement accuracy.

The above object can be achieved by a sensor part of a blood flowmeter for measuring a value on blood flow in tissue of a living body by emitting light to the tissue of a living body and receiving scattered light from the tissue of a living body, the sensor part including:

a light emitter for emitting light to tissue of a living body; and a light detector for receiving the scattered light from the tissue of a living body;

wherein the light emitter and the light detector are integrated on a semiconductor substrate.

According to the invention, since optical fibers are not used, the blood flowmeter can be downsized, and measurement result is not affected by vibration of the optical fibers so that blood flow speed can be measured accurately. In addition, since it is not necessary to assemble optical parts three-dimensionally, manufacturing cost is low. In addition, since the light emitter and the light detector can be integrated monolithically on the same semiconductor substrate, the blood flowmeter can be further small.

The sensor part may further include an optical waveguide on the semiconductor substrate for outputting light emitted from the light emitter to the tissue of a living body by converting the light emitted from the light emitter into convergent light or parallel light.

According to the invention, light suitable for measurement can be emitted so that measurement accuracy can be improved.

The sensor part may further include a first shading block on the semiconductor substrate for preventing light emitted from the light emitter from directly entering the light detector.

According to the invention, scattered light from red blood cells moving in capillaries in tissue of a living body can be detected efficiently and more accurate output can be obtained.

The sensor part may further include a second shading block on the semiconductor substrate in front of the light detector, the second shading block having a predetermined gap.

According to the invention, receiving light area for the light detector can be optimized so that unnecessary scattered light is shielded. Thus, accurate measurement becomes possible.

In the sensor part, an edge-illuminated refracting-facet photodiode is used as the light detector. Accordingly, allowance for shift of optical axis in the up and down direction becomes large. In addition, receiving light area for the light detector can be optimized. Thus, the same effect as using the second shading block can be obtained.

In the sensor part, a DFB laser diode which emits light having a wavelength of about 1.3 μm is used as the light emitter. Accordingly, the light can reach deep part of subcutaneous tissue so that pulse wave of good S/N ratio can be detected.

In the sensor part, the optical waveguide is formed by using fluorinated polyimide. Since the fluorinated polyimide is heat-resistant and chemical-resistant, the optical waveguide becomes suitable for integration process of the sensor chip.

The above object is also achieved by a blood flowmeter for measuring a value on blood flow in tissue of a living body by emitting light to the tissue of a living body and receiving scattered light from the tissue of a living body, the blood flowmeter including a sensor part, the sensor part including:

a light emitter for emitting light to tissue of a living body; and a light detector for receiving the scattered light from the tissue of a living body;

wherein the light emitter and the light detector are integrated on a semiconductor substrate.

The blood flowmeter may further include:

a circuit for driving the light emitter; and a digital signal processor for calculating the value on blood flow by processing signals received from the sensor part.

According to the invention, the whole size of the blood flowmeter can be downsized so that wearable blood flowmeter can be provided.

The blood flowmeter may further include:

a circuit for driving the light emitter; and a circuit for transmitting signals output from the sensor part by wireless.

According to the invention, blood flow amount and the like of many people can be obtained by processing signals sent by wireless in the center.

BRIEF DESCRIPTION OF THE DRAWINGS

Other objects, features and advantages of the present invention will become more apparent from the following detailed description when read in conjunction with the accompanying drawings, in which:

FIGS. 5A and 5B shows a sensor chip according to a third embodiment of the present invention;

FIG. 11 is a block diagram showing another example of a blood flowmeter of the present invention;

DETAILED DESCRIPTION OF THE PREFERRED EMBODIMENTS

In the blood flowmeter of the present invention, a small sensor chip in which components such as a light emitter and a light detector are integrated on a semiconductor substrate is used. By adopting such configuration, manufacturing cost can be lowered by eliminating three-dimensional positioning and assembling. In addition, since the optical fiber can be removed from the structure, the blood flowmeter hardly receives effects from environmental change.

Figure 2:
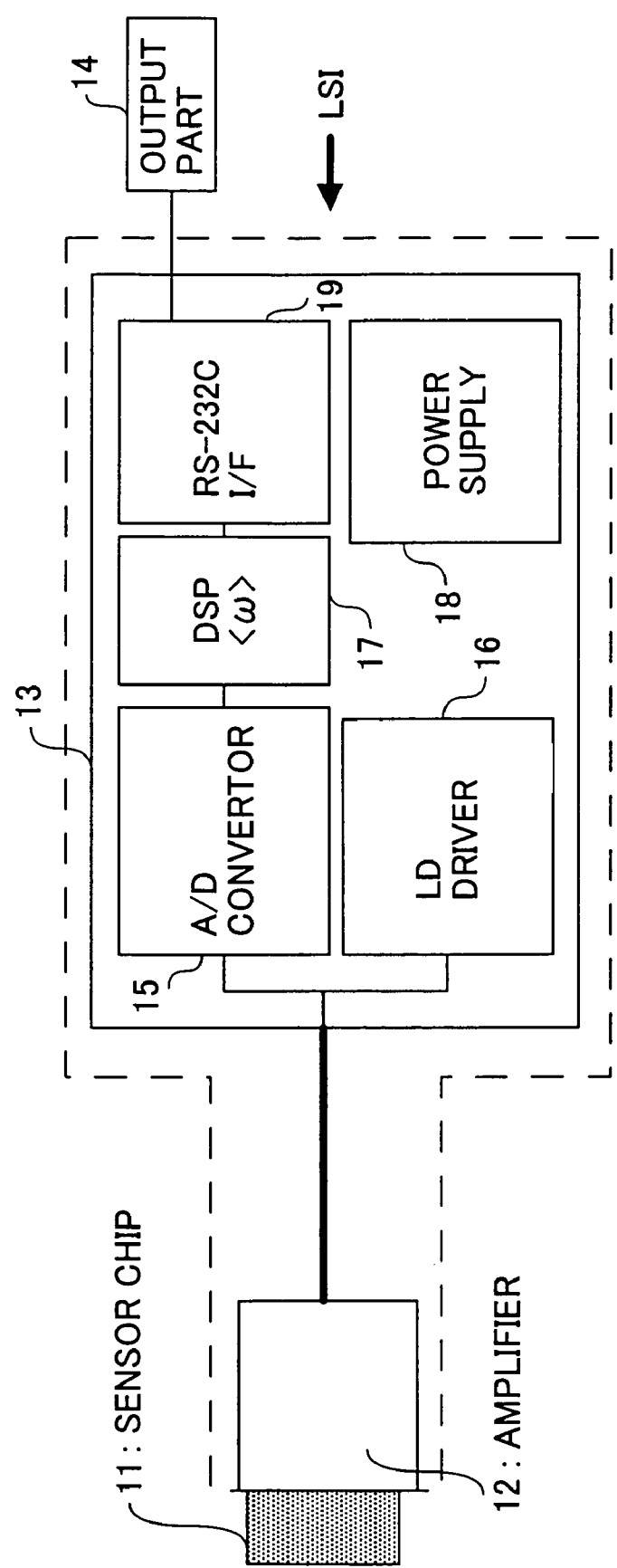
FIG. 2 is a block diagram of an embodiment of a blood flowmeter of the present invention.

FIG. 2 is a block diagram of an embodiment of the blood flowmeter of the present invention. As shown in the figure, the blood flowmeter includes the sensor chip 11 which illuminates tissue of a living body and receives scattered light reflected from the tissue, an amplifier 12 which amplifies the received light, a driving/computing unit 13 for obtaining blood flow by analyzing the scattered light, an output part 14 which displays the obtained blood flow and the like. As will be described later, the sensor chip 11 is integrated on a semiconductor substrate, and the size is about 2 mm×3 mm.

In addition, the driving/computing unit 13 includes an A/D converter 15, an LD driver 16, a digital signal processor (DSP) 17 for calculating blood flow from the received signal, a power supply part 18 and an interface 19, and is connected to the output part 14 which is a small liquid crystal display and the like. The driving/computing unit 13 can be configured as an LSI, and can be integrated with the sensor chip and the amplifier as an blood flowmeter so that the blood flowmeter can be easily attached to a human body.

Figures 3A, 3B:
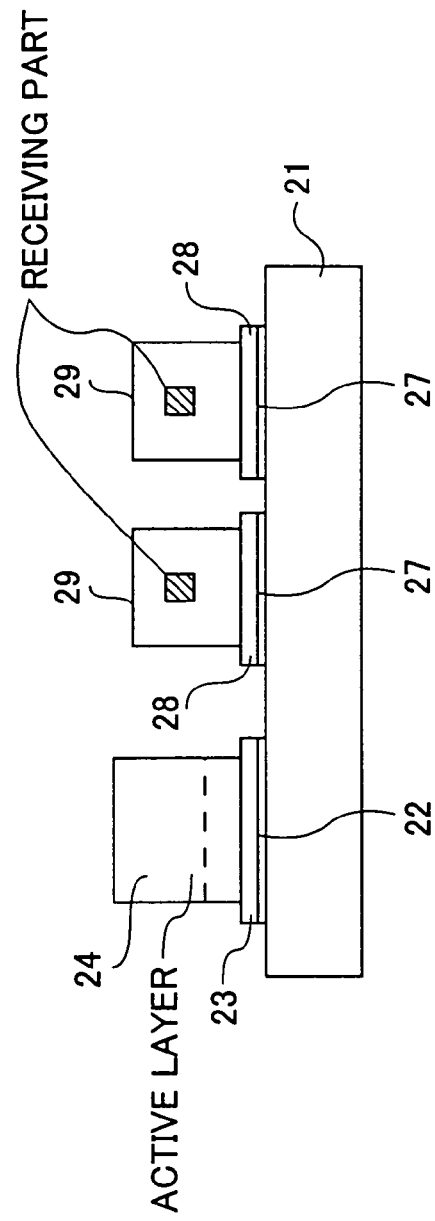
FIGS. 3A and 3B shows a sensor chip according to a first embodiment of the present invention.

FIGS. 3A and 3B show a part (the sensor chip) of the blood flowmeter of a first embodiment of the present invention. FIG. 3A shows a plan, and FIG. 3B shows an A–A' section view. As shown in the figures, in the sensor chip of the first embodiment, an electrode 22 is formed on a semiconductor substrate 21 formed by Si, a semiconductor laser 24 which is a light emitter is formed on the electrode 22 via a solder film 23, a photodiode 26 for auto power control is formed on the electrode 22 on a solder film 25, an electrode 27 is formed on the semiconductor substrate 21, and a photodiode 29 which is the light detector is formed on the electrode 27 in the solder film 28. The photodiode 29 is a part of a measuring part for obtaining a blood flow amount, a blood amount, a blood flow speed and a pulse in tissue of a living body by receiving scattered light reflected from the tissue of the living body. The semiconductor laser 24 and the light detector 29 are bonded accurately on the semiconductor substrate. For bonding the components on the semiconductor substrate accurately, a technique disclosed in Japanese laid-open patent application No. 9-55393 can be used. The size of the semiconductor substrate is about 2 mm long×3 mm wide. The size of other embodiments is the same.

According to this sensor chip, the semiconductor laser 24 oscillates by passing a current through the semiconductor laser 24. At this time, the photodiode 26 provided on one end of the semiconductor laser 24 monitors output of the semiconductor laser 24, and a feedback circuit controls the current passed through the semiconductor laser 24 so that the power of laser oscillation of the semiconductor laser 24 becomes constant. Light emitted from the semiconductor laser 24 propagates in space while spreading in a horizontal direction indicated by the broken lines of FIG. 3A and in a vertical direction. When bringing the semiconductor laser 24 near to the tissue of the living body such as skin, scattered light is generated and the scattered light is entered into the photodiode 29. The scattered light includes an interference component between scattered light reflected from still tissue of the living body and scattered light reflected from red blood cells moving in capillaries of the tissue of the living body, that is, scattered light whose frequency is shifted due to the Doppler effect related to blood flow speed. Therefore, the blood flow speed and the like can be obtained by frequency-analyzing the signal. The measurement using the Doppler shift itself is conventionally known.

It was recognized that linear relationship between the flow speed and Doppler shift frequency holds true by using a solution in which impalpable particles are scattered. The intensity of the scattered light corresponds to an amount of flowing blood, and a blood flow amount can be obtained by multiplying a blood flow speed and a blood mount. In addition, since scattered signal waveform includes modulation component of a pulse, the pulse can be detected.

The optical devices such as the semiconductor laser and the photodiode can be formed monolithically on a GaAs substrate or an InP substrate.

Since the blood flowmeter using the sensor chip does not include the optical fibers, it can be downsized. In addition, since it is unnecessary to handle the optical fibers, it is easy to attach the blood flowmeter to a living body for a long time and it is easy to move with the blood flowmeter on. Further, the blood flowmeter hardly receives effects of environmental change so that the blood flow speed and the like can be obtained accurately.

In addition, since the semiconductor laser 24, the photodiode 26 and the photodiode 29 are formed on the semiconductor substrate 21, the optical parts can be assembled two-dimensionally. Thus, it is not necessary to assemble the optical parts three-dimensionally, and tuning and adjusting the optical axis is not necessary. Therefore, the manufacturing cost is low.

Figure 4A:
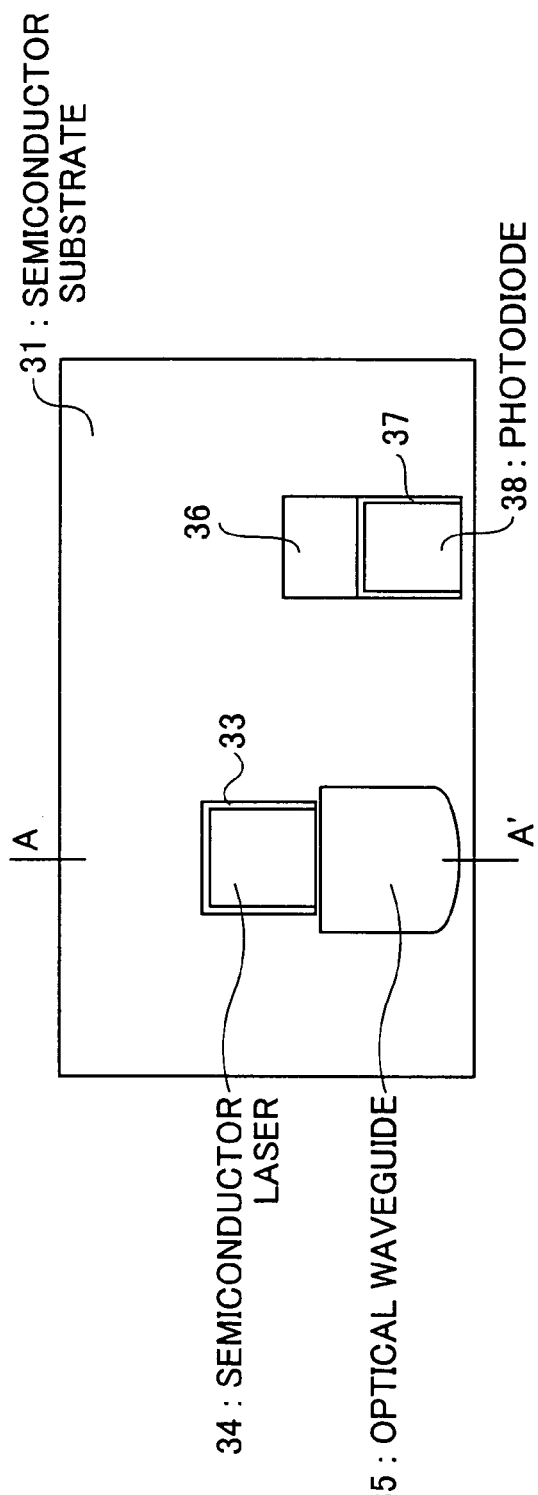
FIGS. 4A and 4B shows a sensor chip according to a second embodiment of the present invention.
Figure 4B:
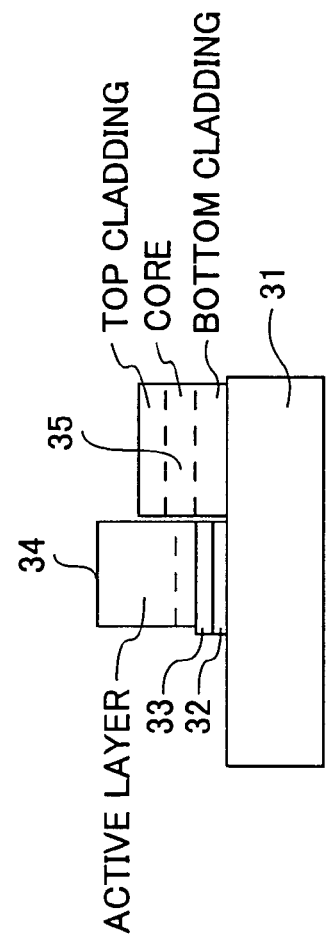

FIGS. 4A and 4B show an example of the sensor chip of a second embodiment of the present invention. FIG. 4A shows a plan, and FIG. 4B shows an A–A' section view. As shown in the figure, in the sensor chip of the second embodiment, an electrode 32 is formed on a semiconductor substrate 31 formed by Si, a semiconductor laser 34 which is a light emitter is formed on the electrode 32 via a solder film 33, and an optical waveguide 35 which is connected to the end face of the semiconductor laser 34 is formed on the semiconductor substrate 31. The optical waveguide 35 is made of fluorinated polyimide, and includes three layers of a bottom cladding, a core and a top cladding. The semiconductor laser 34 is bonded such that the height of an active layer of the semiconductor laser 34 is almost the same as the height of the center of the core of the optical waveguide 35. The optical waveguide 35 outputs light emitted from the semiconductor laser 34 to the tissue of the living body by converting the light into convergent light or parallel light according to an end shape of the optical waveguide 35. In addition, an electrode 36 is formed on the semiconductor substrate 31, a photodiode 38 which is a light detector is formed on the electrode 36 via the solder film 37. The photodiode 38 is a part of a measuring part for obtaining a blood flow amount, a blood amount, a blood flow speed and a pulse in tissue of a living body by receiving scattered light reflected from the tissue of the living body.

Next, a manufacturing method of the optical waveguide 35 will be described. First, a polyamide acid solution is coated on the semiconductor substrate 31 in a desired thickness by spin coat, and, then, the coated film is baked for imidization. After that, a silicone base resist is coated on the polyimide film, and desired patterning is performed on the resist by photolithography. Then, the polyimide film is selectively etched by reactive ion etching in an atmosphere of oxygen by using the resist as a etching mask.

According to the blood flowmeter, the optical waveguide propagates light emitted from the semiconductor laser 34 while confining the light in the vertical direction, and converts the light into the convergent light or the parallel light in the horizontal direction. Thus, since the light can be applied to the outside tissue of the living body as the convergent light state of the parallel light state, proper light can be applied to the tissue of the living body. In addition, since the optical waveguide 35 is made of fluorinated polyimide, the optical waveguide 35 becomes heat-resistant and chemical-resistant so that the optical waveguide 35 becomes suitable for integration process of the sensor chip.

In addition, like the first embodiment, it is possible to oscillate the semiconductor laser in a constant power by providing a photodiode for auto power control. The operation is the same as that of the first embodiment.

FIGS. 5A and 5B shows an example of the sensor chip of a third embodiment of the present invention. FIG. 5A shows a plan, and FIG. 5B shows an A–A' section view. As shown in the figure, in the sensor chip of the third embodiment, an electrode 42 is formed on a semiconductor substrate 41 formed by Si, a semiconductor laser 44 which is a light emitter is formed on the electrode 42 via a solder film 43, and an optical waveguide 45 which is connected to the end face of the semiconductor laser 44 is formed on the semiconductor substrate 41. The optical waveguide 45 is made of fluorinated polyimide, and includes three layers of a bottom cladding, a core and a top cladding. The semiconductor laser 44 is bonded such that the height of an active layer of the semiconductor laser 44 is almost the same as the height of the center of the core of the optical waveguide 45.

In addition, an electrode 46 is formed on the semiconductor substrate 41, a photodiode 48 which is a light detector is formed on the electrode 46 via the solder film 47. The photodiode 48 is a part of a measuring part for obtaining a blood flow amount, a blood amount, a blood flow speed and a pulse in tissue of a living body by receiving scattered light reflected from the tissue of the living body.

In addition, an electrode 49 is formed between the semiconductor laser 44 and the photodiode 48 on the semiconductor substrate 41, and a first shading block 51 for preventing light emitted from the semiconductor laser 44 from directly entering the photodiode 48 is formed on the electrode 49 via the solder film 50. And, an electrode 52 is formed between the photodiode 48 on the semiconductor substrate 41 and the end of the semiconductor substrate 41, and two second shading blocks 54 for cutting off unnecessary scattered light are formed on the electrode 52 via the solder film 53. By providing the two shading blocks such that the interval between the two shading blocks is about 65 μm, a signal having good S/N ratio (signal to noise ratio) can be obtained.

According to such blood flowmeter, the light emitted from the semiconductor laser 44 is prevented from directly entering the photodiode 48 by the shading block 51. In addition, unnecessary scattered light is prevented from directly entering the photodiode 48 by the shading blocks 54. Therefore, blood flow speed can be detected with reliability even when the scattered light reflected from the red blood cells moving in the capillaries in the tissue of the living body is weak, that is, even when the scattered light which received Doppler shift Δf is weak.

These shading blocks can be formed on the semiconductor substrate by bonding accurately. In addition, these shading blocks can be formed by processing the Si substrate by performing wet etching using KOH and the like or by performing dry etching using a deep reactive ion etching apparatus and the like. In addition, a plate in which a slit or a pin hole is formed beforehand can be bonded on the semiconductor substrate as the shading block 54.

Figure 6:
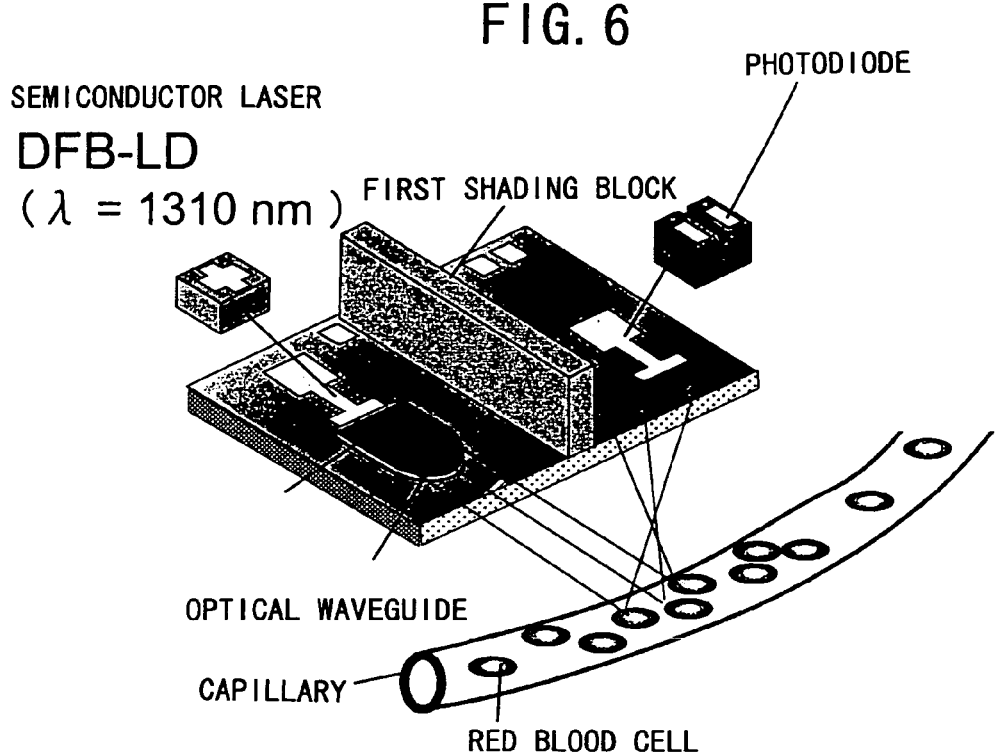
FIG. 6 is a perspective view for explaining a manufacturing method of the sensor chip of the third embodiment.
Figure 7:
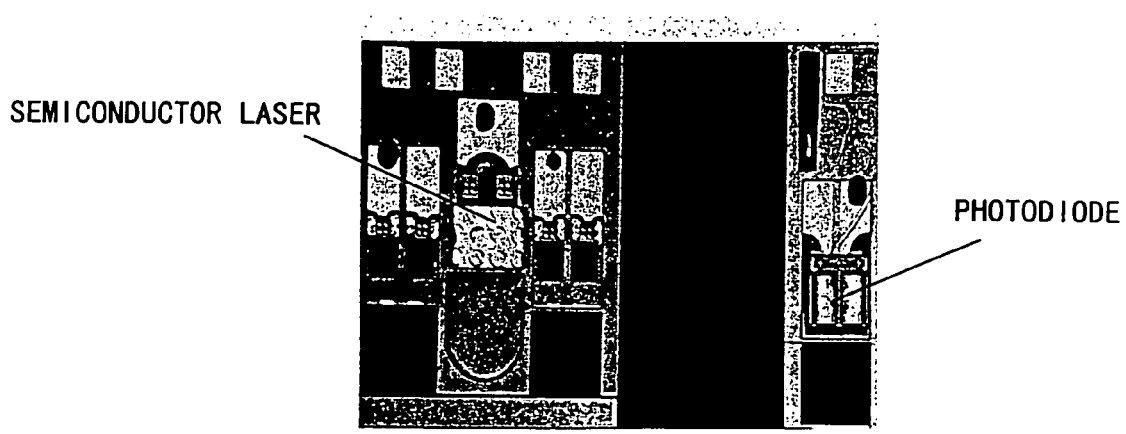
FIG. 7 shows a photomicrograph of the sensor chip generated by the above-mentioned method.

FIG. 6 is a perspective view for explaining a manufacturing method of the sensor chip of the third embodiment, wherein the shading block 54 is not shown in FIG. 6. As shown in the figure, a semiconductor laser (DFB-LD) which is the light emitter and the light detector (photodiode) are bonded accurately on an Si semiconductor substrate on which electrodes and a solder film are patterned. According to this sensor chip, the photodiode detects interference component between scattered light reflected from still tissue of the living body and scattered light (Doppler shifted) reflected from the red blood cells moving in the capillaries in the living body so that the blood flow speed and the like can be obtained. FIG. 7 shows a photomicrograph of the sensor chip fabricated by the above-mentioned method.

Figure 8A:
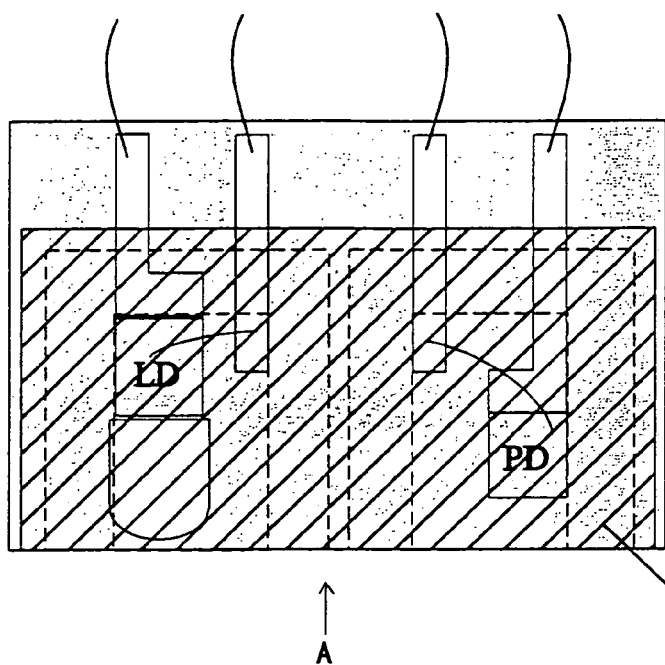
FIGS. 8A–8C show another example of a shading block.
Figure 8C:
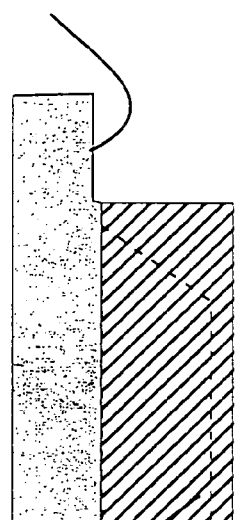
Figure 8B:
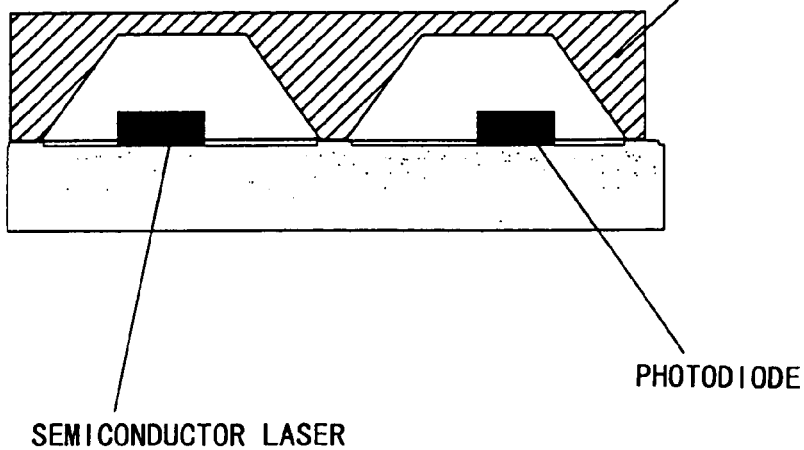

FIGS. 8A–8C show another example of the shading block. FIG. 8A is a top view in which the diagonally shaded area indicates the shading block, FIG. 8B is a front view viewed from A and FIG. 8C is a side view viewed from B. In this example, the shading block is formed such that each of the light emitter (LD) and the light detector (PD) is covered for shielding unnecessary scattered light, and the shading block is bonded on the substrate. By forming the shading block such that it covers the light emitter (LD) and the light detector (PD), the effect of shielding becomes larger. A shading block with a slit which corresponds to the second shading block can be provided on the front of the photodiode in the shading block shown in FIGS. 8A–8C.

Figure 9:
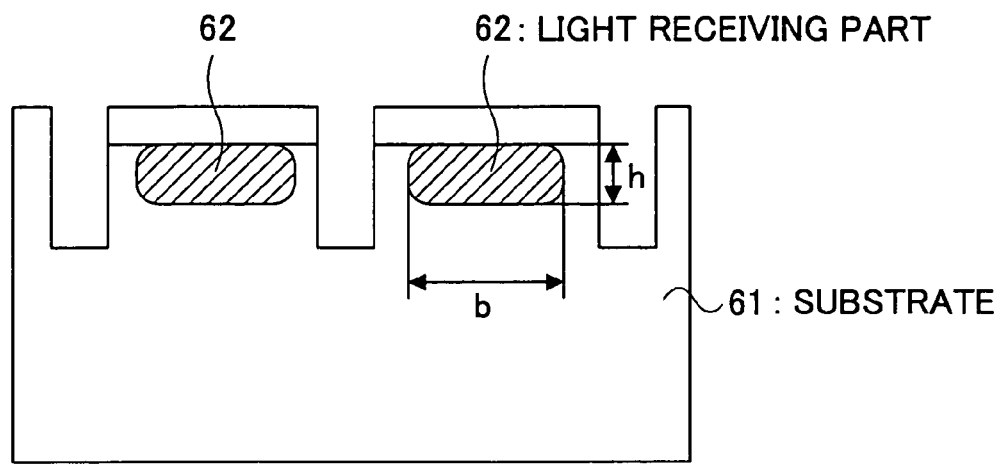
FIG. 9 shows a front view of a photodiode which is used as the light detector of the sensor chip of the blood flowmeter of the present invention.
Figure 10:
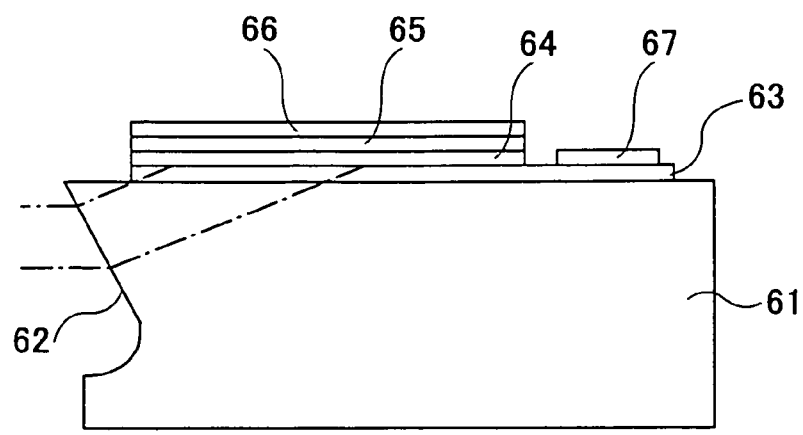
FIG. 10 shows a side view of the photodiode shown in FIG. 9.

FIG. 9 shows a front view of the photodiode which is used as the light detector of the sensor chip of the blood flowmeter of the present invention, and FIG. 10 shows a side view of the photo diode shown in FIG. 9. This photodiode is an edge-illuminated refracting-facet photodiode.

As shown in the figures, a light receiving part 62 which has a light entering end face of an inverse mesa structure is formed on the side of a substrate 61 which is made of InP. The width b of the receiving part 62 is about 65 μm and the height h is 15 μm. In addition, a semiconductor film 63 made of InGaAsP of n type is formed on the substrate 61, a light absorption layer 64 made of InGaAs is formed on the semiconductor film 63, a laminated layer 65 in which InGaAsP of p type, InP of p type and InGaAs of p+ type are laminated is formed on the light absorption layer 64, an electrode 66 of p type is formed on the laminated layer 65, and an electrode 67 of n type is formed on the semiconductor film 63.

For example, H. Fukano, Y. Matsuoka, A Low-Cost Edge-Illuminated Refracting-Facet Photodiode Module with Large Bandwidth and High Responsivity, J. Lightwave Technology, Vol. 18, No. 1, 79–83 (2000) discloses such a photodiode.

In the sensor chip having the photodiode, light shown by alternate long and short dashed lines in FIG. 10 enters the light receiving part 62 from side direction, the light is refracted at the incident end face, is absorbed by the light absorption layer 64 so that the light is converted into an electrical signal. Therefore, allowance for shift of optical axis in the up and down direction is large, and absorption efficiency is large. In addition, since the receiving area is limited, unnecessary scattered light is prevented from entering the photodiode by optimizing the position of the light receiving part 62. Thus, blood flow speed can be detected with reliability even when the scattered light reflected from the red blood cells moving in the capillaries in the tissue of the living body is weak, that is, even when the scattered light whose frequency is shifted due to the Doppler effect is weak. In addition, by narrowing the receiving area, it becomes possible that change of the tissue of the living body can be detected clearly. Therefore, measurement accuracy improves.

In the above-mentioned embodiments, although semiconductor substrates 21, 31, 41 made of Si are used, a semiconductor substrate made of GaAs, InP and the like can also be used. In addition, although optical waveguides 35, 45 made of fluorinated polyimide are used in the above embodiments, the material of the optical waveguide is not limited to organic base substances such as the polyimide. A quartz base optical waveguide and the like can be used. In addition, in the embodiment shown in FIGS. 4 and 5, the photodiode for auto power control can be used like the embodiment shown in FIG. 3.

In the above-mentioned embodiments, a Fabry-Perot laser with a wavelength of 980 nm, a DFB laser with a wavelength of 1.3 μm and a Fabry-Perot laser with a wavelength of 1.3 μm can be used. Especially, as for the light of a wavelength of 1.3 μm, transmittance to skin tissue is higher than that of the light of a wavelength of 780 nm which is widely used for a conventional blood flowmeter on the market. Thus, deep subcutaneous blood flow can be detected so that blood flow waveform having a good S/N ratio can be measured. In addition, the DFB laser is stable and Peltier element is not necessary for cooling.

By providing adjustment marks to the light emitter, the light detector, first and second shading blocks and the semiconductor substrate, and bonding the light emitter, the light detector, first and second shading blocks on the semiconductor substrate by using the adjustment marks, it becomes possible that the light emitter, the light detector, and first and second shading blocks can be bonded on the semiconductor substrata accurately. The Japanese laid-open patent application No. 9-55393 discloses the technology for bonding a light emitter and a light detector on the semiconductor substrate accurately.

Figure 1:
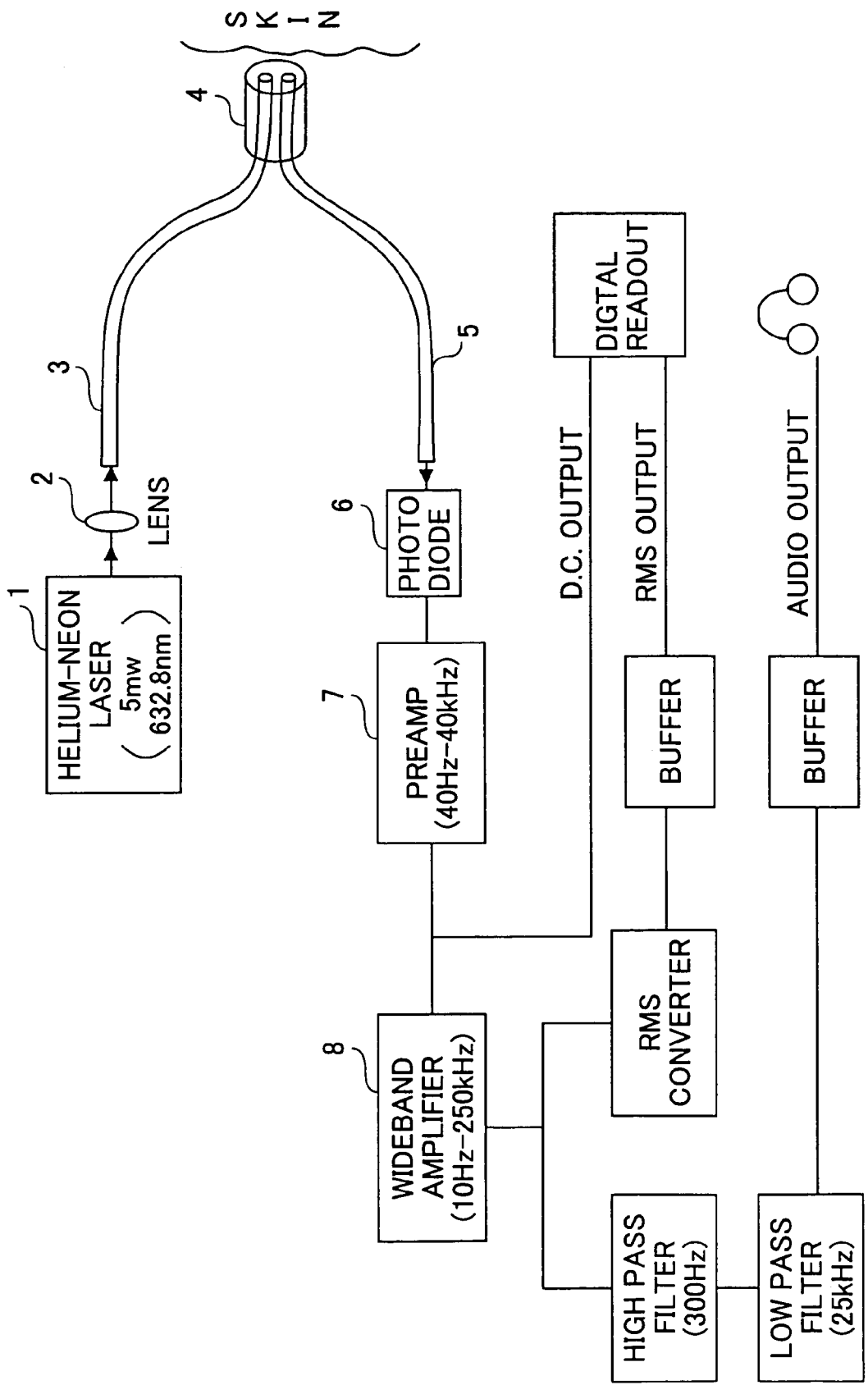
FIG. 1 is a block diagram of a conventional blood flowmeter.

The whole structure of the blood flowmeter having the sensor chip of the present invention is not limited to that shown in FIG. 1. Various other structures can be formed. For example, as shown in FIG. 11, the blood flowmeter can be downsized by placing a PD 71, an LD 72, an optical waveguide 73, an LD/PD driver IC 74, an AD converter/wireless transmitter 75 and a power source battery 76 on the same substrate in which a measured data signal is sent to the center by wireless. The center can obtain blood flow speed and the like of a person who wears the blood flowmeter by using the signal. According to this structure, an ultrasmall and lightweight wearable sensor for a living body which does not cause a feeling of wearing for the user can be realized.

Figure 12A:
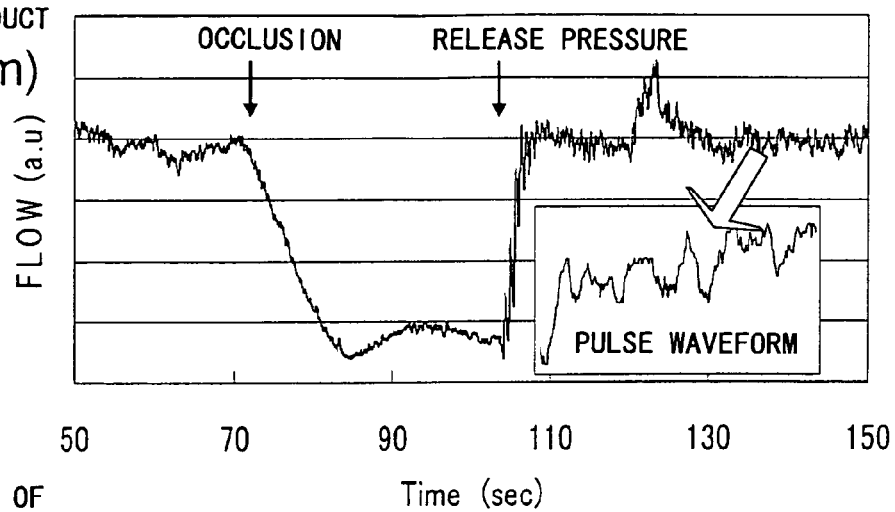
FIGS. 12A and 12B show a result of comparing the blood flowmeter of the present invention with a conventional product.
Figure 12B:
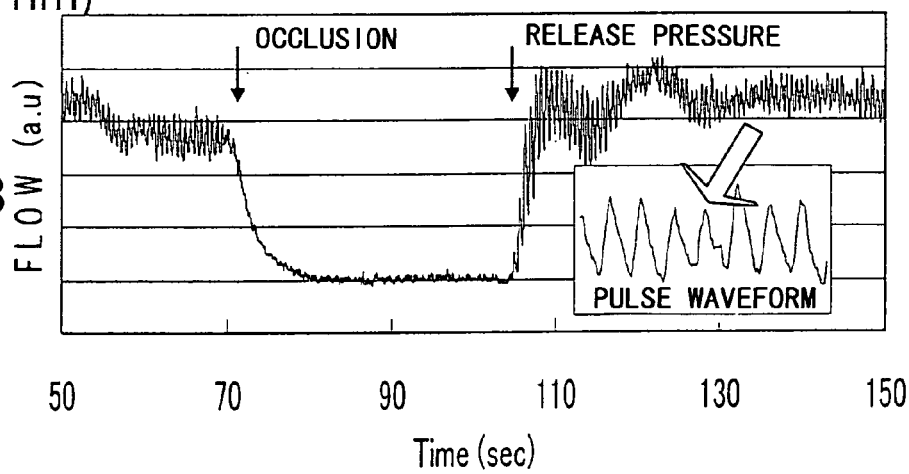

FIGS. 12A and 12B are figures showing the result of comparing the blood flowmeter of the present invention with a conventional product. FIG. 12A indicates output waveform of a conventional commercial blood flowmeter (Cyber Med CDF-1000 of OAS Corporation), and FIG. 12B indicates output waveform of the blood flowmeter of the present invention. These waveforms indicate results of measurement of blood flow of the same part of the same person. The lateral axis indicates time, and the vertical axis indicates blood flow.

In the measurement, pressure is applied on blood-vessel of the root of an arm, and, then, the pressure is released. As shown in FIGS. 12A and 12B, the states of change of blood flow in which the blood flow is decreased by applying pressure and is increased by releasing the pressure are approximately the same. However, pulse waveform which is a magnified view of a part of the graph for the present invention is better-shaped which is closer to an actual pulse than that by the conventional commercial product.

This is because the light of a wavelength of 1.3 μm used in the present invention has higher skin transmittancy than that of the conventional blood flow meter. Therefore, the light can reach deep part of subcutaneous tissue so that more scattered light (light which received Doppler shift) can be received from the blood flow.

As mentioned above, according to the blood flowmeter of the present invention, since optical fibers are not used and the light emitter and the light receiver are integrated on the same semiconductor substrate, downsizing can be realized. In addition, it becomes possible that a person can wear the blood flowmeter for a long time since it is small and light. In addition, accuracy of measurement is not affected by vibration of optical fibers and the like so that accurate blood flow speed measurement can be realized. Further, since it is not necessary to assemble the optical parts three-dimensionally, manufacturing cost is low.

In addition, since the shading block and the photodiode are provided on the same substrate, receiving light area of the photodiode can be optimized and unnecessary scattered light is shielded. Thus, accurate measurement can be realized. In addition, the light leaked from the light emitter can be prevented from directly entering the photodiode by using the shading block. As a result, scattered light (received Doppler shift) reflected from the red blood cells moving in capillaries in the living body can be detected efficiently so that more accurate output can be obtained.

In addition, by using a laser of a wavelength of 1.3 μm, 980 nm or 850 nm which is longer than that of a laser of the conventional product for the semiconductor laser of the power source, the light can be allowed to pass through the subcutaneous tissue to a deep part. Thus, well-shaped waveform can be detected.

The present invention is not limited to the specifically disclosed embodiments, and variations and modifications may be made without departing from the scope of the invention. for scanning.

What is claimed is:

1. A sensor part of a blood flowmeter for measuring a value on blood flow in tissue of a living body by emitting light to said tissue of a living body and receiving scattered light from said tissue of a living body, wherein the value on blood flow is calculated based on Doppler shifts in the scattered light, said sensor part comprising:
    a light emitter for emitting light to tissue of a living body, wherein said light emitter is a laser diode which emits light having a wavelength of about 1.3 μm;
    a light detector for receiving said scattered light from said tissue of a living body;
    a first shading structure on said semiconductor substrate for preventing light emitted from said light emitter from directly entering said light detector; and
    a second shading structure on said semiconductor substrate in front of said light detector, said second shading structure having a predetermined gap;
    wherein said light emitter and said light detector are integrated on a semiconductor substrate, and the sensor part includes an optical waveguide on said semiconductor substrate for outputting light emitted from said light emitter to said tissue of a living body by converting said light emitted from said light emitter into convergent light or parallel light, wherein said optical waveguide includes a bottom cladding, a core and a top cladding, and the light emitted from said light emitter propagates through the core, and
    wherein a ratio of said predetermined gap of said second shading structure to a lateral length of the semiconductor substrate is about 2%.

2. The sensor part as claimed in claim 1, wherein said light emitter and said light detector are monolithically integrated on said semiconductor substrate.

3. The sensor part as claimed in claim 1, wherein an edge-illuminated refracting-facet photodiode is used as said light detector.

4. The sensor part as claimed in claim 1, wherein said laser diode is a DFB laser diode.

5. The sensor part as claimed in claim 1, wherein said optical waveguide is formed by using fluorinated polyimide.

6. The sensor part as claimed in claim 1, wherein said value on blood flow is a blood flow amount, a blood amount, a blood flow speed or a pulse.

7. The sensor part as claimed in claim 1, wherein the light emitter is a semiconductor laser, and the semiconductor laser is bonded to the semiconductor substrate such that the height of an active layer of the semiconductor laser is almost the same as the height of the center of the core of the optical waveguide.

8. A blood flowmeter for measuring a value on blood flow in tissue of a living body by emitting light to said tissue of a living body and receiving scattered light from said tissue of a living body, said blood flowmeter comprising a sensor part and a processor that receives a signal from the sensor part and computes the value on blood flow based on Doppler shifts in the scattered light, said sensor part comprising:
    a light emitter for emitting light to tissue of a living body, wherein said light emitter is a laser diode which emits light having a wavelength of about 1.3 μm;
    a light detector for receiving said scattered light from said tissue of a living body;
    a first shading structure on said semiconductor substrate for preventing light emitted from said light emitter from directly entering said light detector; and
    a second shading structure on said semiconductor substrate in front of said light detector, said second shading structure having a predetermined gap;
    wherein said light emitter and said light detector are integrated on a semiconductor substrate, and the sensor part includes an optical waveguide on said semiconductor substrate for outputting light emitted from said light emitter to said tissue of a living body by converting said light emitted from said light emitter into convergent light or parallel light, wherein said optical waveguide includes a bottom cladding, a core and a top cladding, and the light emitted from said light emitter propagates through the core, and
    wherein a ratio of said predetermined gap of said second shading structure to a lateral length of the semiconductor substrate is about 2%.

9. The blood flowmeter as claimed in claim 8, said blood flowmeter further comprising:
    a circuit for driving said light emitter.

10. The blood flowmeter as claimed in claim 8, said blood flowmeter further comprising:
    a circuit for driving said light emitter; and
    a circuit for wirelessly transmitting signals output from said sensor part.

11. The blood flowmeter as claimed in claim 8, wherein the light emitter is a semiconductor laser, and the semiconductor laser is bonded to the semiconductor substrate such that the height of an active layer of the semiconductor laser is almost the same as the height of the center of the core of the optical waveguide.

12. The blood flowmeter as claimed in claim 8, wherein said optical waveguide is formed by using fluorinated polyimide.

13. The blood flowmeter as claimed in claim 8, wherein an edge-illuminated refracting-facet photodiode is used as said light detector.

14. A sensor part of a blood flowmeter for measuring a value on blood flow in tissue of a living body by emitting light to said tissue of a living body and receiving scattered light from said tissue of a living body, wherein the value on blood flow is calculated based on Doppler shifts in the scattered light, said sensor part comprising:
   a light emitter for emitting light to tissue of a living body, wherein said light emitter is a laser diode which emits light having a wavelength of about 1.3 µm;
   a light detector for receiving said scattered light from said tissue of a living body;
   a first shading structure on said semiconductor substrate for preventing light emitted from said light emitter from directly entering said light detector; and
   a second shading structure on said semiconductor substrate in front of said light detector, said second shading structure having a predetermined gap;
   wherein said light emitter and said light detector are integrated on a semiconductor substrate, and the sensor part includes an optical waveguide on said semiconductor substrate for outputting light emitted from said light emitter to said tissue of a living body by converting said light emitted from said light emitter into convergent light or parallel light, wherein said optical waveguide includes a bottom cladding, a core and a top cladding, and the light emitted from said light emitter propagates through the core, and
   wherein said predetermined gap of said second shading structure is about 65 µm.

15. The A blood flowmeter for measuring a value on blood flow in tissue of a living body by emitting light to said tissue of a living body and receiving scattered light from said tissue of a living body, said blood flowmeter comprising a sensor part and a processor that receives a signal from the sensor part and computes the value on blood flow based on Doppler shifts in the scattered light, said sensor part comprising:
   a light emitter for emitting light to tissue of a living body, wherein said light emitter is a laser diode which emits light having a wavelength of about 1.3 µm;
   a light detector for receiving said scattered light from said tissue of a living body;
   a first shading structure on said semiconductor substrate for preventing light emitted from said light emitter from directly entering said light detector; and
   a second shading structure on said semiconductor substrate in front of said light detector, said second shading structure having a predetermined gap;
   wherein said light emitter and said light detector are integrated on a semiconductor substrate, and the sensor part includes an optical waveguide on said semiconductor substrate for outputting light emitted from said light emitter to said tissue of a living body by converting said light emitted from said light emitter into convergent light or parallel light, wherein said optical waveguide includes a bottom cladding, a core and a top cladding, and the light emitted from said light emitter propagates through the core, and
   wherein said predetermined gap of said second shading structure is about 65 µm.

16. A sensor part of a blood flowmeter for measuring a value on blood flow in tissue of a living body by emitting light to said tissue of a living body and receiving scattered light from said tissue of a living body, wherein the value on blood flow is calculated based on Doppler shifts in the scattered light, said sensor part comprising:
   a light emitter for emitting light to tissue of a living body; and
   a light detector for receiving said scattered light from said tissue of a living body;
   wherein said light emitter and said light detector are integrated on a semiconductor substrate,
   said sensor part further comprising a first shading structure on said semiconductor substrate for preventing light emitted from said light emitter from directly entering said light detector, and a second shading structure on said semiconductor substrate in front of said light detector, said second shading structure having a predetermined gap,
   wherein the sensor part includes an optical waveguide on said semiconductor substrate for outputting light emitted from said light emitter to said tissue of a living body by converting said light emitted from said light emitter into convergent light or parallel light, wherein said optical waveguide includes a bottom cladding, a core and a top cladding, and the light emitted from said light emitter propagates through the core, and
   wherein a ratio of said predetermined gap of said second shading structure to a lateral length of the semiconductor substrate is about 2%.

17. The sensor part as claimed in claim 16, wherein an edge-illuminated refracting-facet photodiode is used as said light detector.

18. The sensor part as claimed in claim 16, wherein said optical waveguide is formed by using fluorinated polyimide.

19. The sensor part as claimed in claim 16, wherein the light emitter is a semiconductor laser, and the semiconductor laser is bonded to the semiconductor substrate such that the height of an active layer of the semiconductor laser is almost the same as the height of the center of the core of the optical waveguide.

20. A sensor part of a blood flowmeter for measuring a value on blood flow in tissue of a living body by emitting light to said tissue of a living body and receiving scattered light from said tissue of a living body, wherein the value on blood flow is calculated based on Doppler shifts in the scattered light, said sensor part comprising:
   a light emitter for emitting light to tissue of a living body; and
   a light detector for receiving said scattered light from said tissue of a living body;
   wherein said light emitter and said light detector are integrated on a semiconductor substrate,
   said sensor part further comprising a first shading structure on said semiconductor substrate for preventing light emitted from said light emitter from directly entering said light detector, and a second shading structure on said semiconductor substrate in front of said light detector, said second shading structure having a predetermined gap,
   wherein the sensor part includes an optical waveguide on said semiconductor substrate for outputting light emitted from said light emitter to said tissue of a living body by converting said light emitted from said light emitter into convergent light or parallel light, wherein said optical waveguide includes a bottom cladding, a core and a top cladding, and the light emitted from said light emitter propagates through the core, and wherein said predetermined gap of said second shading structure is about 65 μm.

21. A blood flowmeter for measuring a value on blood flow in tissue of a living body by emitting light to said tissue of a living body and receiving scattered light from said tissue of a living body, said blood flowmeter comprising a sensor part and a processor that receives a signal from the sensor part and computes the value on blood flow based on Doppler shifts in the scattered light, said sensor part comprising:

a light emitter for emitting light to tissue of a living body; and a light detector for receiving said scattered light from said tissue of a living body;

wherein said light emitter and said light detector are integrated on a semiconductor substrate, said sensor part further comprising a first shading structure on said semiconductor substrate for preventing light emitted from said light emitter from directly entering said light detector, and a second shading structure on said semiconductor substrate in front of said light detector, said second shading structure having a predetermined gap, wherein a ratio of said predetermined gap of said second shading structure to a lateral length of the semiconductor substrate is about 2%, and wherein the sensor part includes an optical waveguide on said semiconductor substrate for outputting light emitted from said light emitter to said tissue of a living body by converting said light emitted from said light emitter into convergent light or parallel light, wherein said optical waveguide includes a bottom cladding, a core and a top cladding, and the light emitted from said light emitter propagates through the core.

22. The blood flowmeter as claimed in claim 21, said blood flowmeter further comprising:

a circuit for driving said light emitter.

23. The blood flowmeter as claimed in claim 21, said blood flowmeter further comprising:

a circuit for driving said light emitter; and a circuit for wirelessly transmitting signals output from said sensor part.

24. The blood flowmeter as claimed in claim 21, wherein the light emitter is a semiconductor laser, and the semiconductor laser is bonded to the semiconductor substrate such that the height of an active layer of the semiconductor laser is almost the same as the height of the center of the core of the optical waveguide.

25. The blood flowmeter as claimed in claim 21, wherein said optical waveguide is formed by using fluorinated polyimide.

26. The blood flowmeter as claimed in claim 21, wherein an edge-illuminated refracting-facet photodiode is used as said light detector.

27. A blood flowmeter for measuring a value on blood flow in tissue of a living body by emitting light to said tissue of a living body and receiving scattered light from said tissue of a living body, said blood flowmeter comprising a sensor part and a processor that receives a signal from the sensor part and computes the value on blood flow based on Doppler shifts in the scattered light, said sensor part comprising:

a light emitter for emitting light to tissue of a living body; and a light detector for receiving said scattered light from said tissue of a living body;

wherein said light emitter and said light detector are integrated on a semiconductor substrate, said sensor part further comprising a first shading structure on said semiconductor substrate for preventing light emitted from said light emitter from directly entering said light detector, and a second shading structure on said semiconductor substrate in front of said light detector, said second shading structure having a predetermined gap, wherein the sensor part includes an optical waveguide on said semiconductor substrate for outputting light emitted from said light emitter to said tissue of a living body by converting said light emitted from said light emitter into convergent light or parallel light, wherein said optical waveguide includes a bottom cladding, a core and a top cladding, and the light emitted from said light emitter propagates through the core;

wherein said predetermined gap of said second shading structure is about 65 μm.

* * * * *